(12) United States Patent
Mikhailov et al.

(10) Patent No.: US 8,761,334 B2
(45) Date of Patent: Jun. 24, 2014

(54) METHOD FOR DETERMINING SPATIAL DISTRIBUTION AND CONCENTRATION OF CLAY IN A CORE SAMPLE

(75) Inventors: Dmitry Mikhailov, Moscow (RU); Alexander Nikolaevich Nadeev, Spring, TX (US); Valery Vasilievich Shako, Domodedovo (RU); Nikita Ilyich Ryzhikov, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 13/531,347

(22) Filed: Jun. 22, 2012

(65) Prior Publication Data
US 2013/0010919 A1 Jan. 10, 2013

(30) Foreign Application Priority Data

Jun. 23, 2011 (RU) ................................ 2011125731

(51) Int. Cl.
*G01N 23/06* (2006.01)

(52) U.S. Cl.
USPC .......................................................... 378/53

(58) Field of Classification Search
CPC .................................................... G01N 23/046
USPC ............ 378/45, 48, 49, 50, 51, 53, 55, 56, 57
See application file for complete search history.

(56) References Cited

U.S. PATENT DOCUMENTS

| | | | |
|---|---|---|---|
| 4,540,882 | A | 9/1985 | Vinegar et al. |
| 4,649,483 | A | 3/1987 | Dixon |
| 4,688,238 | A | 8/1987 | Sprunt et al. |
| 4,722,095 | A | 1/1988 | Muegge et al. |
| 4,982,086 | A | 1/1991 | Withjack |
| 5,027,379 | A | 6/1991 | Hunt et al. |
| 5,469,488 | A | 11/1995 | Ono |
| 2005/0010106 | A1 | 1/2005 | Lang et al. |

FOREIGN PATENT DOCUMENTS

| | | |
|---|---|---|
| RU | 2207808 C2 | 7/2003 |
| RU | 2360233 C1 | 6/2009 |

*Primary Examiner* — Courtney Thomas

(57) ABSTRACT

A water-soluble salt of a metal with a high atomic weight is selected as an X-ray contrast substance providing a selective ion-exchange reaction with a clay. The salt has a general formula $R^+M^-$, where $R^+$ is selected from a group consisting of $Ba^{2+}$; $Sr^{2+}$; $Tl^+$; $Rb^+$ ..., and $M^-$ is selected from a group consisting of $Cl_n$; $NO_n$; OHn; CH3COO, $SO_4$; .... The X-ray contrast substance is injected into a core sample. Upon completion of the selective ion exchange reaction a non-contrast displacing agent is injected into the sample. The sample is scanned by computer X-ray microtomography. An area of interest and a reference cross-section are selected at the obtained computer tomography image. Grayscale histograms in cross-sections of the sample are obtained. Spatial distribution and concentration of the clay is estimated by means of histograms analysis starting from the reference cross-section histogram.

4 Claims, 3 Drawing Sheets

METHOD FOR DETERMINING SPATIAL DISTRIBUTION AND CONCENTRATION OF CLAY IN A CORE SAMPLE

CROSS-REFERENCE TO RELATED APPLICATION

This application claims priority to Russian Patent Application Serial No. RU 2011125731 filed 23 Jun. 2011, which is incorporated herein by reference in its entirety.

FIELD OF THE DISCLOSURE

The disclosure is related to methods for determining spatial distribution and concentration of natural clay in a core sample or concentration of clay which penetrated the core during drilling mud injection.

BACKGROUND OF THE DISCLOSURE

There is a problem of formation damage caused by a drilling mud (or a flush liquid) especially for long horizontal wells since most of them are completed uncased, i.e., without a cemented and perforated flow string.

Drilling muds are complex mixtures of clay, fine particles (sized from several millimeters to less than one micron) and organic additives (polymers, surfactants etc.) contained in a "carrying" liquid—a drilling mud "base" such as water, oil or some synthetic liquid.

During a drilling process, a drilling mud filtrate with fines and clay contained therein penetrate a formation near a wellbore area. The formation near the wellbore area is under an excessive pressure and this causes a signifcant reduction of the permeability of the formation (to characterize this phenomenon the term "damage of the formation near-wellbore area" or just "formation damage" is used).

During a clean-up process (by means of gradual production starting) these components (e.g., fines and clay) are partially washed out of the near-wellbore area and its permeability partially recovers. However, a part of the components remains in pore space of the formation (absorbed on a pore surface, captured by pore throats etc.), which results in significant difference between recovered and initial permeabilities (normally, the recovered permeability does not exceed 50-70% of the initial).

A common laboratory method for checking drilling mud quality is to direct and reverse filtration through a core sample during which dynamics of permeability reduction/recovery are measured as a function of a number of injected pore volumes of the drilling mud or oil (the latter—in case of reverse pumping simulating the cleanup process).

However, clay and other drilling mud components distribution and concentration retained in the pore space along a core sample is important information for understanding mechanism of formation damage and selection of a relevant method for improving a productivity index (minimization of a bottomhole formation zone damage). These parameters are not measured in a conventional procedure for determining drilling mud quality.

One of the most well known methods for non-destructive sample analysis is an X-ray computer tomography. Thus, U.S. Pat. No. 4,540,882 describes a method for determining a drilling mud invasion using a core X-ray computer tomography with a contrast agent addition. The first material is added to the drilling mud in order to obtain a first fluid having an effective atomic number different from an effective atomic number of connate fluids contained in a formation borehole zone. A preserved core sample is collected from the borehole for scanning by a computer axial tomographic X-ray scanner to determine attenuation coefficients at a plurality of points in a cross section of the core sample. The core sample is scanned using X-rays at first and second energies. The determined attenuation coefficients for the plurality of points located in the cross section at each energy are used to determine an atomic number image for the cross section of the core sample. The depth of invasion of the first fluid is then determined from the atomic number image, as an indicator of the depth of invasion of the drilling fluid into the core sample.

Another method is disclosed in U.S. Pat. No. 4,722,095. It is based on a high X-ray attenuation coefficient of barite widely used as a weighting agent in drilling mud. First, a mud filtrate is removed from a core sample after which pore and total volume of the core sample as well as the volume of barite particles that penetrated the sample are measured using X-ray computer tomography.

Unfortunately, the use of barite as a contrast agent to evaluate the drilling mud penetration depth is not always justified because the size of these particles is comparable with the size of pore throats and, consequently, most of them will be captured in small pores near the sample inlet.

Other drilling mud components (clay, polymers, water etc.) have a weak X-ray contrast and cannot have spatial definition with the required accuracy.

The use of a contrast agent soluble in a "carrying fluid," as it was described in U.S. Pat. No. 5,027,379, does not enable to evaluate penetration depth as well as concentration of clay and other mildly-contrasting additives contained in the drilling mud because the penetration depth of the drilling mud filtrate and the said additives is different.

SUMMARY OF THE DISCLOSURE

The disclosed method provides for an enhanced accuracy of determination of spatial distribution and concentration of clay in a core sample due to an improved X-ray contrast of a clay during computer X-ray tomography of core samples and the analysis of histograms of the image.

A contrast X-ray substance is injected into a core sample. The contrast X-ray substance is a water-soluble salt of a metal with a high atomic weight providing a selective ion-exchange reaction with a clay. The metal water-soluble salt has a general formula $R^+M^-$, where $R^+$ is selected from a group consisting of $Ba^{2+}$; $Sr^{2+}$; $Tl^+$; $Rb^+$ ..., and $M^-$ is selected from a group consisting of $Cl_n^-$; $NO_n^-$; $OHn$; $CH3COO$, $SO_4^-$; .... Substances $R^+$ and $M^+$ are selected as per a standard table of inorganic substances water solubility.

Upon completion of the selective ion exchange reaction a non-contrasting displacing agent is injected into the core sample and the core sample is scanned by means of an X-ray tomography. A computer tomography image of the core sample is obtained and an area of interest and a reference cross-section are selected at the obtained computer tomography image. Grayscale histograms in cross-sections of the sample are obtained. Spatial distribution and concentration of clay in the sample are determined by means of histograms analysis starting from the reference cross-section histogram.

In one of the embodiments of the invention the histograms are analyzed as follows. A quantity of different materials presented in the area of interest in the reference cross-section of the computer tomography image of the core sample is determined as a number of spikes at the reference cross-section histogram.

Knowing an X-ray radiation absorption coefficient of the metal used in the contrast substance a spike corresponding to the clay modified after interaction with the contrast substance is identified at the reference cross-section histogram.

The reference cross-section histogram $I_i(z)$ for each separate material is approximated using normal distribution (Gaussian function)

$$I_i^1(z) = A_i^1 \exp\left[-\left(\frac{z - B_i^1}{C_i^1}\right)^2\right]$$

where i is a material index;
I—a total number of pixels with a grayscale value of z;
$A_i$, $B_i$, $C_i$—Gaussian adjustable parameters.

The Gaussian adjustable parameters' values are roughly evaluated for all the materials presented at the reference cross-section histogram in the area of interest. The Gaussian adjustable parameters are accurately evaluated by means of minimization of a modulus of difference between a real histogram in the area of interest at the reference cross-section and the sum of normal distributions corresponding to separate materials $$\sum_{j=1}^{M}\left[H^1(z_j) - \sum_{i=1}^{N} A_i^1 \exp\left(-\left(\frac{z_j - B_i^1}{C_i^1}\right)^2\right)\right] \to 0$$

where j—a histogram grayness range index;
M—a total number of grayness ranges;
N—a total number of the materials presented at a cross-section of the obtained computer tomographic image.

The obtained Gaussian adjustable parameters $A_i^1$, $B_i^1$, $C_i^1$ are used as initial parameters for minimization of a modulus of difference between the real histogram in the area of interest and a sum of normal distributions corresponding to separate materials for a next cross-section of the obtained computer tomographic image of the core sample. For each next cross-section of the computer tomographic image of the core sample Gaussian adjustable parameters obtained for the preceding cross-section are used as initial parameters. A relative quantity of a certain material for each cross-section is determined using Gaussian integration:

$$a_i^k = \int A_i^k \exp\left[-\left(\frac{z - B_i^k}{C_i^k}\right)^2\right] dz,$$

where k=1 . . . K—a number of a tomographic image cross-section.

Applying this procedure to each cross-section of the obtained computer tomographic image (k=1 . . . K) concentration profiles of all contrast components along an axis of the core sample are obtained. From the obtained concentration profiles a profile corresponding to the clay modified after interaction with the contrast substance is selected.

In another embodiment of the invention the histograms are analyzed as follows.

Inside the area of interest on the reference cross-section sub-areas are selected, each of the sub-areas containing only one specific material and histograms of separate materials are obtained. All the histograms are normalized by their areas. The histograms of separate materials are brought to a common scale.

Knowing an X-ray absorption coefficient of a metal used in the contrast substance, a grayscale corresponding to the clay modified after interaction with the contrast substance is determined. Based on this grayscale the material in the cross section corresponding to the clay is identified.

A histogram of the entire area of interest on the reference cross-section is approximated using the sum of normalized histograms of separate materials with weight factors corresponding to areas occupied by the separate materials on this cross-section of the obtained computer tomographic image of the core sample. Weight factors of minimization of a modulus of difference between a real histogram in the area of interest on the reference cross-section and the sum of histograms of separate materials are determined $$\left[\sum_{j=1}^{M}(|A_j^1 - b^1 B_j^1 - c^1 C_j^1 - \ldots|)\right] \to 0$$

where $A_j$, $B_j$, $C_j$, . . . —are the bars with numerical data of the histograms;
b, c, d—weight factors for the histograms;
j—a grayscale index in a histogram;
M—a total number of grayness ranges.

Applying the preceding step to all cross-sections of the obtained computer tomographic image of the core sample, concentration profiles for all contrast components along an axis of the core sample are obtained. From the obtained concentration profiles a profile corresponding to the clay modified after interaction with the contrast substance is selected.

DETAILED DESCRIPTION

If a water-soluble salt of metal with a high atomic weight capable of entering into a selective ion-exchange reaction with a clay is used as an X-ray contrast substance, heavy metal ions are accumulated on the clay thus increasing its contrast to X-ray radiation. As a result of injecting a non-contrast displacing agent into the sample after the selective ion exchange reaction remaining heavy metal salts and reaction products are washed out of the core sample.

As an example of the invention embodiment let us consider the use of the method claimed for the determination of the increase of contrast to an X-ray radiation for the clay retained in a pore volume after the cycle direct-reverse filtration of a model drilling mud (2% water solution of bentonite clay) through the core sample.

Filtration experiment on the injection of a bentonite clay 2% water solution and subsequent washout of the penetrated clay from a porous medium (reverse injection) is performed. After the end of the experiment, only clay strongly retained in the pore bottlenecks (pore traps) remains in the sample pore volume.

A water-soluble salt of a metal with a high atomic weight entering a selective ion-exchange reaction with a clay in question is selected as a contrast substance. Accounting for the bentonite clay composition $Al_2[Si_4O_{10}](OH)_2 \cdot nH_2O$ and following a standard table of inorganic substances solubility in water $BaCl_2$ is selected as the metal salt.

Figure 1:
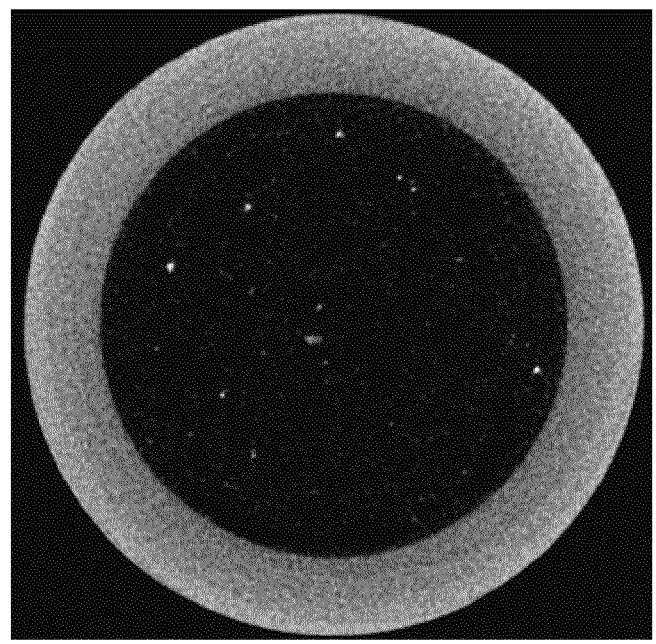
FIG. 1 shows data of computer X-ray microtomography of an initial clay water solution (before mixing with a contrast substance) and of a contrast clay water solution.
Figure 1:
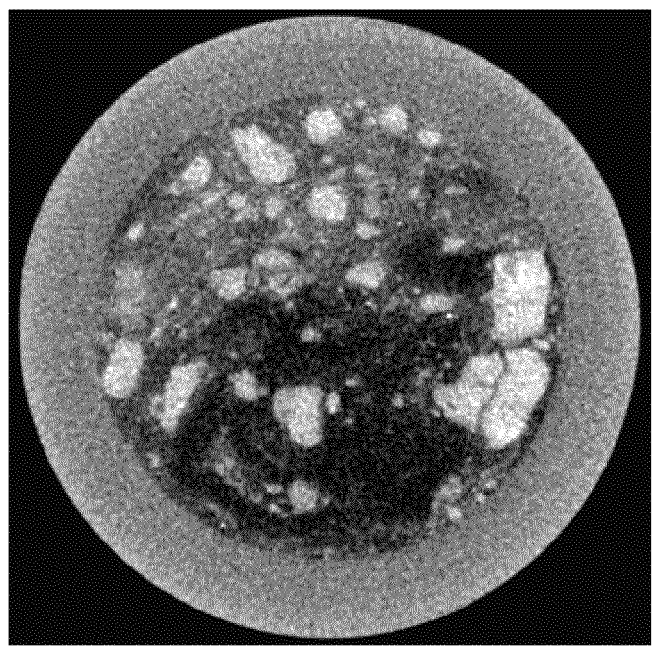
Figure 2:
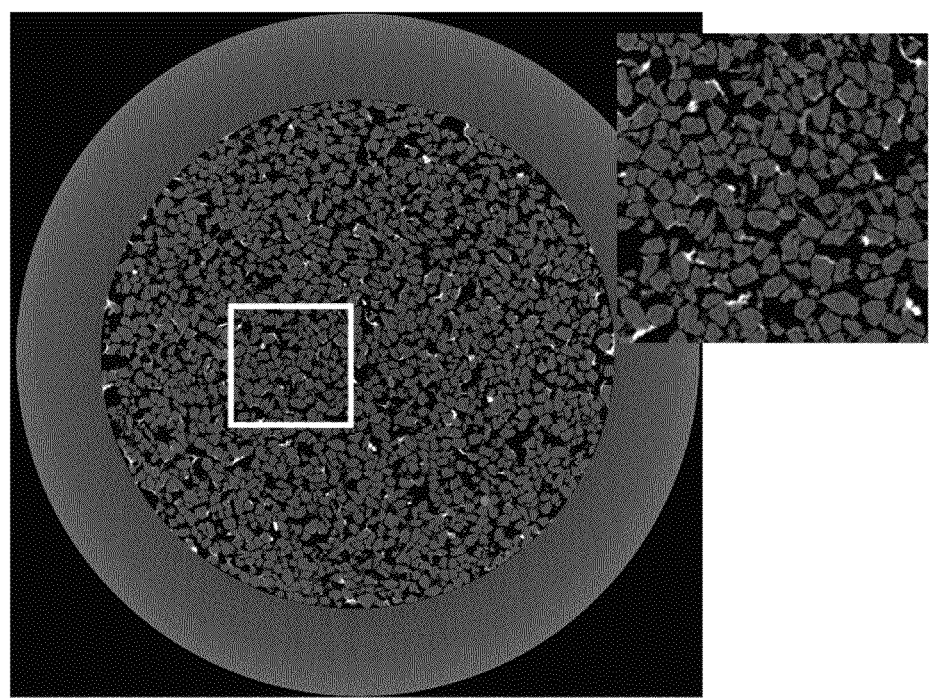
FIG. 2 shows an example of computer X-ray microtomography of a sample after the injection of the contrast substance.

FIG. 1 shows computer X-ray micromography data for a water solution of an initial clay (before mixing with the contrast substance) and a water solution of the contrast clay (i.e., clay that underwent ion-exchange reaction with $BaCl_2$ salt).

The sample is saturated with water solution of the contrast substance ($BaCl_2$) and held for some time dependent on the reaction rate. At the end of the reaction, 3-4 pore volumes of a model non-contrasting fluid (salt solution) are pumped through the sample to remove reaction products and contrast substance residues. An injection rate must not exceed a rate of the reverse pumping in the filtration experiment.

The sample is scanned using computer X-ray microtomography. In an obtained computer tomography image of the sample an area of interest and a reference cross-section are selected.

The area of interest corresponds to a sub-area of the obtained three-dimensional computer tomography image which is selected for subsequent analysis. This sub-area is selected, for example, because it includes some specific peculiarities (microcracks, microinclusions, defects, etc.) or merely as a typical representative scope of the complete tomographic image of an object if the analysis of the complete image required too much time and computing efforts.

The reference cross-section of the computer tomography image is understood as a typical cross-section containing the area of interest from which for this particular problem it is most convenient to begin the analysis (for example, the first cross-section).

Histograms of grayscale distribution in cross-sections of the sample are obtained, for example, using ImageJ software tool (cf. http://rsbweb.nih.gov/ij/).

A quantity of different materials presented in the area of interest on the reference cross-section of the computer tomographic image of the sample is determined as a number of spikes on the reference cross-section histogram.

Knowing an X-ray radiation absorption coefficient of a metal used in the contrast substance, a spike corresponding to the clay modified after interaction with the contrast substance is identified on the reference cross-section histogram. A clay index is designated as $i_{cn}$.

A histogram $I_i(z)$ of the reference cross-section for each separate material is approximated using normal distribution (Gaussian function)

$$I_i^1(z) = A_i^1 \exp\left[-\left(\frac{z - B_i^1}{C_i^1}\right)^2\right]$$

where i is a material index;
I—a total number of pixels with a grayscale value of z;
$A_i$, $B_i$, $C_i$—Gaussian adjustable parameters;

The Gaussian adjustable parameters' values are roughly evaluated for all the materials presented at the reference cross-section histogram in the area of interest. The Gaussian adjustable parameters are accurately evaluated by means of minimization of a modulus of difference between a real histogram in the area of interest at the reference cross-section and a sum of normal distributions corresponding to separate materials $$\sum_{j=1}^{M}\left[H^1(z_j) - \sum_{i=1}^{N} A_i^1 \exp\left(-\left(\frac{z_j - B_i^1}{C_i^1}\right)^2\right)\right] \to 0$$

where j—the histogram grayness range index;
M—a total number of grayness ranges;
N—a total number of the materials presented at the cross-section of the computer tomographic image.

The obtained Gaussian adjustable parameters $A_i^1$, $B_i^1$, $C_i^1$ are used as initial parameters for minimization of a modulus of difference between a real histogram in the area of interest and a sum of normal distributions corresponding to separate materials relating to a next cross-section of the tomographic image. For each next tomographic image cross-section the Gaussian adjustable parameters obtained for a preceding cross-section are used as initial parameters. A relative quantity (concentration) of a certain material for each cross-section is determined using Gaussian integration:

$$a_i^k = \int A_i^k \exp\left[-\left(\frac{z - B_i^k}{C_i^k}\right)^2\right] dz,$$

where k=1 ... K—a number of a cross-section of the computer tomographic image of the core sample.

Applying this procedure to each cross-section of the computer tomographic image (k=1 ... K) concentration profiles of all contrast components along an axis of the sample are obtained. From the obtained concentration profiles a profile corresponding to a material with the index $ii_{cn\pi}$, i.e., clay modified after the interaction with the contrast substance is selected.

Figure 3:
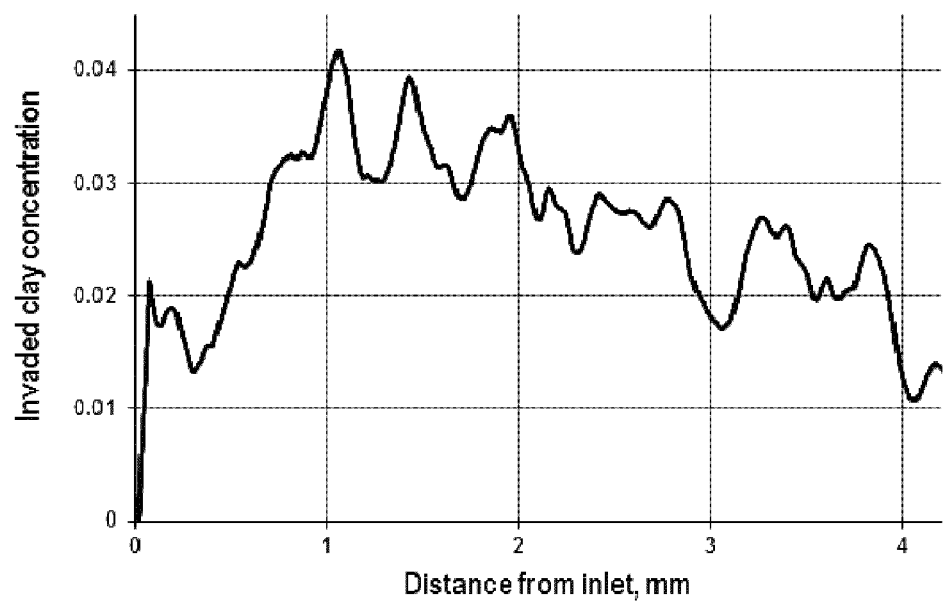
FIG. 3 shows a profile of clay distribution along the sample length obtained using the described histogram analysis method.

FIG. 3 shows clay distribution profile along the sample length obtained using the described histogram analysis method.

In another embodiment of the invention sub-areas are selected inside the area of interest, each sub-area containing only one specific material and histograms of separate materials are obtained. All histograms are normalized by their areas. The histograms of separate materials are brought to a common scale.

Knowing an X-ray absorption coefficient of a metal used in the contrast substance, a grayscale corresponding to the clay modified after interaction with the contrast substance is determined. Based on this grayscale a material in the cross section corresponding to the clay is identified. The clay index is designated as $ii_{cn\pi}$.

A histogram of the entire area of interest at the reference cross-section is approximated using a sum of normalized histograms of separate materials with weight factors corresponding to the areas occupied by separate substances on this cross-section of the computer tomographic image. Weight factors of minimization of a modulus of difference between a real histogram in the area of interest on the reference cross-section and a sum of histograms of separate materials are determined $$\left[\sum_{j=1}^{M} (|A_j^1 - b^1 B_j^1 - c^1 C_j^1 - \ldots|)\right] \to 0$$

where $A_j$, $B_j$, $C_j$, ... —are the bars with numerical data of the histograms;

b, c, d—weight factors for the histograms;
j—a grayscale index in a histogram;
M—a total number of grayness ranges.

Applying the preceding step to all cross-sections of the computer tomographic image, concentration profiles for all the contrast components along the sample axis are obtained. From the obtained concentration profiles a profile corresponding to a material with the index of $i_{27\pi}$, i.e., clay modified after interaction with the contrast substance is selected.

What is claimed is:

1. A method for determining spatial distribution and concentration of clay in a core sample, the method comprising:
   selecting a water-soluble salt of a metal with a high atomic weight as an X-ray contrast substance providing a selective ion-exchange reaction with the clay, the salt having a general formula $R^+M^-$, where $R^+$ is selected from a group consisting of $Ba^{2+}$; $Sr^{2+}$; $Tl^+$; $Rb^+$ . . . , $M^-$ is selected from a group consisting of $Cl_n$; $NO_n$; OHn; CH3COO, $SO_4$; . . . in accordance with a standard table of inorganic substances' water solubility,
   injecting the X-ray contrast substance into a core sample,
   upon completion of the selective ion exchange reaction injecting a non-contrasting displacing agent into the core sample,
   scanning the sample by computer X-ray microtomography, obtaining a computer tomography image of the core sample,
   selecting an area of interest and a reference cross-section at the obtained computer tomography image of the core sample,
   obtaining grayscale histograms in cross-sections of the core sample and
   determining spatial distribution and concentration of the clay in the core sample by means of histogram analysis starting from the reference cross-section histogram.

2. The method of claim 1 wherein a salt water solution is used as the non-contrasting displacing agent.

3. The method of claim 1 wherein the histogram analysis comprises:
   determining a quantity of different materials presented in the area of interest in the reference cross-section of the obtained computer tomography image of the core sample as a number of spikes at the reference cross-section histogram,
   determining a spike corresponding to the clay modified after interaction with the contrast substance at the reference cross-section histogram,
   approximating the reference cross-section histogram $I_i(z)$ for each separate material using normal distribution (Gaussian function)

$$I_i^1(z) = A_i^1 \exp\left[-\left(\frac{z - B_i^1}{C_i^1}\right)^2\right]$$

where i is a material index;
I—a total number of pixels with a grayscale value of z;
$A_i$, $B_i$, $C_i$—Gaussian adjustable parameters;
   roughly evaluating the Gaussian adjustable parameters' values for all the materials presented at the reference cross-section histogram in the area of interest,
   accurately evaluating the Gaussian adjustable parameters by means of minimization of a modulus of difference between a real histogram in the area of interest at the reference cross-section and a sum of normal distributions corresponding to separate materials $$\sum_{j=1}^{M}\left[H^1(z_j) - \sum_{i=1}^{N} A_i^1 \exp\left(-\left(\frac{z_j - B_i^1}{C_i^1}\right)^2\right)\right] \to 0$$

where j—a histogram grayness range index;
M—a total number of grayness ranges;
N—a total number of the materials presented at the tomographic histogram,
   using the obtained Gaussian adjustable parameters $A_i^1$, $B_i^1$, $C_i^1$ as initial parameters for minimization of a modulus of difference between the real histogram in the area of interest and a sum of normal distributions corresponding to separate materials for a next cross-section of the computer tomographic image of the core sample,
   using Gaussian adjustable parameters obtained for the preceding cross-section as initial parameters for each next cross-section of the computer tomographic image of the core sample,
   determining a relative quantity of a certain material for each cross-section by Gaussian integration:

$$a_i^k = \int A_i^k \exp\left[-\left(\frac{z - B_i^k}{C_i^k}\right)^2\right] dz,$$

where k=1 . . . K—a number of a cross-section of the computer tomographic image of the core sample,
   obtaining concentration profiles for all contrast components along an axis of the core sample,
   selecting from the obtained concentration profiles a profile corresponding to the clay modified after interaction with the contrast substance.

4. The method of claim 1 wherein the histogram analysis comprises:
   selecting sub-areas inside the area of interest in the reference cross-section of the computer tomography image of the core sample, each sub-area containing only one specific material,
   obtaining histograms of separate materials,
   normalizing the histograms by their areas,
   bringing the histograms of separate materials to a common scale,
   determining a grayscale corresponding to the clay,
   approximating the histogram of the area of interest on the reference cross-section by a sum of the normalized histograms of separate materials with weight factors corresponding to areas occupied by separate substances on this cross-section in the computer tomographic image of the core sample,
   determining weight factors of minimization of a modulus of difference between a real histogram in the area of interest on the reference cross-section and a sum of the histograms of separate materials as $$\left[\sum_{j=1}^{M}(|A_j^1 - b^1 B_j^1 - c^1 C_j^1 - \ldots|)\right] \to 0$$

where $A_j$, $B_j$, $C_j$, . . . —are the bars with numerical data of the histograms;
b, c, d—weight factors for the histograms;
j—a grayscale index in a histogram;
M—a total number of grayness ranges, applying the preceding step to all cross-sections of the computer tomographic image of the core sample,
obtaining concentration profiles for all contrast components along an axis of the core sample,
selecting from the obtained concentration profiles a profile corresponding to the clay modified after interaction with the contrast substance.

\* \* \* \* \*